US011828717B1

(12) United States Patent
Li et al.

(10) Patent No.: US 11,828,717 B1
(45) Date of Patent: Nov. 28, 2023

(54) METHOD FOR EVALUATING AND UTILIZING SONNENBRAND BASALT AGGREGATE

(71) Applicant: RESEARCH INSTITUTE OF HIGHWAY MINISTRY OF TRANSPORT, Beijing (CN)

(72) Inventors: Mingliang Li, Beijing (CN); Jun Li, Beijing (CN); Hao Wu, Beijing (CN)

(73) Assignee: RESEARCH INSTITUTE OF HIGHWAY MINISTRY OF TRANSPORT, Beijing (CN)

( * ) Notice: Subject to any disclaimer, the term of this patent is extended or adjusted under 35 U.S.C. 154(b) by 0 days.

(21) Appl. No.: 18/322,669

(22) Filed: May 24, 2023

(30) Foreign Application Priority Data

May 27, 2022 (CN) .......................... 202210594186.2

(51) Int. Cl.
*E01C 23/00* (2006.01)
*G01N 25/00* (2006.01)
(Continued)

(52) U.S. Cl.
CPC ............... *G01N 25/00* (2013.01); *E01C 7/18* (2013.01); *E01C 23/01* (2013.01); *G01N 33/383* (2013.01)

(58) Field of Classification Search
CPC ........ G01N 25/00; G01N 33/383; E01C 7/18; E01C 23/01
(Continued)

(56) References Cited

U.S. PATENT DOCUMENTS 5,453,212 A * 9/1995 Annemaier ........... E01C 11/245
106/788
5,494,741 A * 2/1996 Fekete .................... E01C 7/147
427/407.1
(Continued)

FOREIGN PATENT DOCUMENTS

CN 106908327 A 6/2017
CN 106908383 A 6/2017
(Continued)

OTHER PUBLICATIONS

Li et al. "Comparisons on Road Performance of Porous Asphalt Mixtures with Different High Viscosity Additives" Highway, Feb. 2020, No. 2, 0001-04.
(Continued)

*Primary Examiner* — Raymond W Addie
(74) *Attorney, Agent, or Firm* — Kaplan Breyer Schwarz, LLP; Stuart H. Mayer (57) ABSTRACT

Provided is a method for evaluating and utilizing sonnenbrand basalt aggregate, including steps as follows: mixing a basalt aggregate defined as sonnenbrand basalt into an asphalt mixture; carrying out thermal aging experiments at different temperatures and durations to obtain a theoretical trigger time $t_i$ for the sonnenbrand phenomenon under a thermal aging temperature $T_i$; further calculating to obtain a theoretical thermal aging factor $AF_0$ for the sonnenbrand phenomenon; statistically calculating a thermal aging factor AF for an actual construction to evaluate a performance of the basalt aggregate, if $AF<AF_0$, the construction may be carried out normally, if $AF \geq AF_0$, then shortening the transportation and waiting duration and/or lowering the factory temperature of the asphalt mix so that the thermal aging factor $AF<AF_0$ during actual construction.

8 Claims, 4 Drawing Sheets

(51) Int. Cl.
*E01C 7/18* (2006.01)
*E01C 23/01* (2006.01)
*G01N 33/38* (2006.01)

(58) Field of Classification Search
USPC .................................. 404/17–31, 72–75, 118
See application file for complete search history.

(56) References Cited

U.S. PATENT DOCUMENTS

| | | | | |
|---|---|---|---|---|
| 6,966,723 | B2* | 11/2005 | Zentner | E01C 11/005 404/17 |
| 7,879,921 | B2* | 2/2011 | Cummins | C08L 33/066 521/64 |
| 8,312,690 | B1* | 11/2012 | Klemaske, II | E04F 15/12 404/82 |
| 11,542,667 | B1* | 1/2023 | Ayadat | B32B 27/065 |

FOREIGN PATENT DOCUMENTS

| | | | |
|---|---|---|---|
| CN | 108863132 A | 11/2018 | |
| CN | 112213473 A | 1/2021 | |
| CN | 112255261 A | 1/2021 | |
| CN | 114166684 A * | 3/2022 | .............. G01N 5/04 |
| CN | 114166684 A | 3/2022 | |
| JP | 2001305046 A | 10/2001 | |

OTHER PUBLICATIONS

Zhan Jun1, Sheng Sen2, "Experimental Study on the Performance of Small Particle Size Porous Asphalt Mixture" Highway, Feb. 2019 No. 2, 0248-04.

* cited by examiner

METHOD FOR EVALUATING AND UTILIZING SONNENBRAND BASALT AGGREGATE

CROSS-REFERENCE TO RELATED APPLICATIONS

This application claims priority to Chinese Patent Application No. 202210594186.2, filed on May 27, 2022, the contents of which are hereby incorporated by reference.

TECHNICAL FIELD

The present application relates to the technical field of road construction, and in particular to a method for evaluating and utilizing a sonnenbrand basalt aggregate.

BACKGROUND

Asphalt pavement is one of the main forms of high-grade highways in China, and sand and gravels account for the largest proportion (above 90%) of its constituent materials. Large-scale highway construction and maintenance needs a large amount of sand and gravel materials, and the scientific and reasonable utilization of high-quality stone is an important measure to ensure project quality and resource conservation in China, where high-quality stone resources are in short supply. At present, the asphalt surface layer of high-grade highway in China requires high-quality stone, and the surface layer in particular generally uses basalt crushed stone as coarse aggregate. Basalt contains some special components that are sensitive to temperature, moisture, etc. due to geological action, rock-forming environment, etc., which may cause spots and cracks to gradually appear on the surface of poorly weathered basalt aggregates if exposed to long-term high water immersion at high temperatures or to natural environments such as sun exposure and rain, a phenomenon known as the sonnenbrand phenomenon, or light stripping. Further decay of basalt aggregates with sonnenbrand phenomenon causes surface stone peeling, and in severe cases, larger cracks and aggregate fractures.

Asphalt pavements are subjected to the combined effects of multiple environmental factors such as light, moisture, and temperature during the construction and operation phases, which may trigger the sonnenbrand phenomenon of basalt, causing problems such as chalking of the aggregate surface and peeling of the asphalt coating. Under severe sonnenbrand phenomenon, obvious pavement damage problems such as aggregate raveling appear even after short period of opening to traffic, resulting in rework of the project.

To avoid the sonnenbrand phenomenon of basalt aggregate, there are upper limit standard for basalt aggregate weatherability stipulated in standards such as BS EN 1367-3:2001 Tests for thermal and weathering properties of aggregates: Part 3: Boiling test for Sonnenbrand basalt and China's Technical Specifications for Design and Construction of Porous Asphalt Pavement, and basalt aggregates shall not be used if the weatherability of the basalt is not in compliance with the requirements. According to the EU standard BS EN 1367-3:2001 Tests for thermal and weathering properties of aggregates: Part 3: Boiling test for Sonnenbrand basalt, relevant tests are carried out after 36 hours of continuous boiling of the aggregates to determine whether the basalt aggregates are sonnenbrand basalt. However, the basalt sonnenbrand phenomenon is very sensitive to environmental factors, and the severity of the sonnenbrand phenomenon varies depending on the environmental conditions the basalt is subjected to, or does not even occur when the sonnenbrand phenomenon is not triggered. Therefore, the "upper limit standard" to completely disqualify sonnenbrand basalt may actually cause a large quantity of waste of stone resources. Accordingly, it is very important to evaluate and estimate the paving performance of sonnenbrand basalt aggregate on asphalt pavement, and to ensure that the sonnenbrand phenomenon is not triggered by reasonable control of construction conditions, so as to provide guidance for the standardization and scientific application of basalt aggregate and realize resource saving.

SUMMARY

The present application solves the technical problem that some basalt stones are wasted when the sonnenbrand basalt is evaluated by the prior art, then provides a method for evaluating and utilizing a sonnenbrand basalt aggregate that may reasonably evaluate and estimate the paving performance of sonnenbrand basalt aggregates on asphalt pavements, and ensure that the sonnenbrand phenomenon is not triggered by reasonably controlling the construction conditions.

The technical schemes adopted by the application for solving the technical problems are as follows:

a method for evaluating and utilizing a sonnenbrand basalt aggregate, including steps as follows:

S1, mixing a basalt aggregate defined as a sonnenbrand basalt into an asphalt mixture;

S2, carrying out experiments on several proportions of the asphalt mixture prepared in the S1 under conditions of different thermal aging temperatures and different thermal aging durations, where the experiments are arranged with several groups, and the thermal aging temperatures of the experiments arranged with several groups are in a value range of 150 degrees Celsius (° C.)-190° C. and are selected at equal intervals within the value range of the temperatures, denoted as $T_i$, i=1, 2 . . . , n, and n is a number of experimental groups; in each group of the experiments, a thermal aging duration of each experiment is in a value range of 0 hour (h)-12 h, and is selected respectively at equal intervals within the value range; shaping the asphalt mixture after thermal aging into a Marshall specimen, measuring the specimen in terms of Cantabro raveling loss, and determining a theoretical spot trigger time $t_i$ respectively under different thermal aging temperatures $T_i$ according to a relationship curve of thermal aging duration-raveling loss obtained from each group of experiments;

S3, determining a theoretical thermal aging factor $AF_i$ of the basalt aggregate defined as the sonnenbrand basalt obtained from each group of experiments according to a calculation method as follows:

$$AF_i = T_i \times t_i$$

among them, $AF_i$ is a theoretical thermal aging factor obtained from an $i^{th}$ group experiment, i=1, 2 . . . , n, and n is the number of experimental groups; a minimum value of $AF_i$ is taken as a theoretical thermal aging factor $AF_0$ of the sonnenbrand phenomenon, where:

$$AF_0 = \min\{AF_1 \ldots AF_i \ldots AF_n\}$$

S4, calculating a thermal aging factor AF of an actual construction:

$$AF = T' \times t'$$

among them, T' is an average temperature value of a factory temperature of the actual construction of the asphalt mixture when a material truck leaves a mixing plant and an arrival temperature of the material truck after reaching a site and starting to pave, and t' is a duration for transportation and waiting for the material truck of the asphalt mixture from leaving a factory to arriving at the site to start paving;

S5, evaluating the basalt aggregate in terms of performance, carrying out a construction normally if $AF<AF_0$ when the basalt aggregate is used to pave an upper layer, and shortening the duration for transportation and waiting and lowering the factory temperature of the asphalt mixture if $AF \geq AF_0$ to make the thermal aging factor of the actual construction $AF<AF_0$; and when the basalt aggregate is used to pave other surface layers below the upper layer, carrying out a construction normally if $AF<AF_0$; and if $AF \geq AF_0$, shortening the duration for transportation and waiting and/or lowering the factory temperature of the asphalt mixture to make the thermal aging factor of the actual construction $AF<AF_0$, or adding a waterproof insulation layer above the surface layer In the S1 a method to define the basalt aggregate includes:
a. mixing the basalt aggregate into an asphalt mixture;
b. subjecting the asphalt mixture to thermal aging under a temperature condition of 180° C. for 5 h;
c. cooling the asphalt mixture after finishing the thermal aging to a room temperature, then adding water of room temperature into the asphalt mixture until the asphalt mixture is submerged; and
d. standing for 24 h, taking out the aggregate bonded into lumps out of the water, and gently breaking off by hand to observe whether there is an asphalt coating peeling phenomenon in an appearance of the aggregate, and determining whether the basalt aggregate is a sonnenbrand basalt according to observed results.

As observing whether there is the asphalt coating peeling phenomenon in the appearance of the aggregate, the asphalt coating peeling phenomenon is graded according to a peeling situation of the asphalt coating, with a grading criteria as follows: grade 5, where the asphalt coating is completely preserved, with a percentage of a peeled area close to 0; grade 4, where the asphalt coating is moved by water in a few portions with an uneven thickness, and the percentage of peeled area is less than or equal to 10%; grade 3, where the asphalt coating is obviously moved by water locally, basically retained on a surface of the aggregate, and the percentage of peeled area is less than or equal to 30%; grade 2, where the asphalt coating is largely moved by water, partially remained on the surface of aggregate, and the percentage of the peeled area is greater than 30%; and grade 1, where the asphalt coating is completely moved by water, the aggregate is basically exposed, and the asphalt floats on a water surface; the basalt aggregate is defined as a sonnenbrand basalt if the grade is below 5.

In the S1, when mixing the basalt aggregate defined as sonnenbrand basalt into the asphalt mixture, a production mixture ratio actually adopted in construction is used for mixing.

The asphalt mixture mixed in the S1 is any one of asphalt concrete (AC) mixture, stone matrix asphalt (SMA), open-graded friction course (OGFC) porous asphalt mixture or porous asphalt concrete (PAC) asphalt mixture.

A method for determining the theoretical spot trigger time $t_i$ in the S2 is as follows:

when a raveling loss corresponding to an inflection point of a significantly increased raveling loss in the relationship curve of the thermal aging duration-raveling loss is ≤15%, the thermal aging duration corresponding to the inflection point is the theoretical spot trigger time $t_i$; and when the raveling loss corresponding to the inflection point of the significantly increased raveling loss in the relationship curve of the thermal aging duration-raveling loss is ≥15%, the thermal aging duration corresponding to the raveling loss of 15% is the theoretical spot trigger time $t_i$.

In the S5, as lowering the factory temperature of the asphalt mixture, the factory temperature of the asphalt mixture is lowered by using a warm-mixing technology.

The waterproof insulation layer includes a double-layer structure of a waterproof layer and a thermal insulation layer.

The waterproof layer is any one of emulsified asphalt, hot asphalt, hot asphalt macadam sealing layer and polymer material paving layer.

The insulation layer is any one of material laying layers of rubber, ceramic, rock wool, fiber, foam board, etc.

The method for evaluating and utilizing the sonnenbrand basalt aggregate has the advantages that:

the method for evaluating and utilizing sonnenbrand basalt aggregate of the present application is applicable to the performance evaluation of pavements where the basalt aggregate is designed for use in the upper layer, or where the basalt aggregate is designed for use in the surface layer located below the upper layer, without a waterproof insulation layer; for the use of sonnenbrand basalt asphalt mixture, the trigger conditions for the sonnenbrand phenomenon of basalt are clarified by formulating the asphalt mixture used in construction and conducting thermal aging experiments, and it is suggested that the sonnenbrand phenomenon of basalt is related to the unfavorable components contained in it, and the unfavorable components need certain external conditions for chemical reaction, i.e., a certain temperature and duration before the sonnenbrand phenomenon occurs; the concept and calculation method of thermal aging factor are given by testing the growth pattern of the raveling loss of asphalt mixture under different thermal aging conditions, and the trigger conditions of basalt sonnenbrand phenomenon are clarified by using quantitative thermal aging factor, which may accurately evaluate the paving performance of the sonnenbrand basalt aggregate; when the thermal aging factor of the actual construction is evaluated to be less than the theoretical thermal aging factor of the sonnenbrand phenomenon, it may be determined that the basalt aggregate may be used properly in the construction and meet the performance requirements of the road pavement; whether the thermal aging factor of the actual construction is greater than or equal to the theoretical thermal aging factor of the sonnenbrand phenomenon is evaluated; when the basalt aggregate is used for laying the upper layer, the construction may proceed normally if $AF<AF_0$; if $AF \geq AF_0$, the thermal aging factor $AF<AF_0$ is obtained by shortening the transportation and waiting duration and/or lowering the factory temperature of the asphalt mixture for the actual construction; when the basalt aggregate is used to lay other surface layers located below the upper layer, construction may proceed normally if $AF<AF_0$; if $AF \geq AF_0$, construction can proceed normally by shortening the transportation and waiting duration and/or lowering the factory temperature of the asphalt mixture so that the thermal aging factor $AF<AF_0$ during actual construction, or by adding a waterproof insulation layer above the surface layer; based on the results of the evaluation method, the present application provides guidance on the utilization of basalt aggregates in pavement surfacing construction, ensuring that the basalt aggregates meet the pavement requirements;

according to the method for evaluating and utilizing the sonnenbrand basalt aggregate of the present application, as defining the basalt aggregate, the basalt aggregate is mixed into an asphalt mixture, and subjected to thermal aging under a temperature condition of 180° C. for 5 h, and cooled after finishing the thermal aging to a room temperature, then water of room temperature is added into the asphalt mixture until the asphalt mixture is submerged; and after standing for 24 h, the aggregate bonded into a lump is taken out and gently broken off by hand to observe whether there is the asphalt coating peeling phenomenon in the appearance of the aggregate, and the basalt aggregate is defined as a sonnenbrand basalt if there is peeling off of asphalt coating; compared with the method in the prior art for defining whether an aggregate is a sonnenbrand basalt by continuous boiling for 36 h, the total time spent for the method of the present application is about 30 h, which obviously reduces the testing duration; moreover, the whole test process of defining in this application is conducted at room temperature without open flame, which does not require manual participation, and a quick determination of whether the aggregate is sonnenbrand basalt is obtained by manual observation after water immersion treatment.

To make the technical schemes of the method for evaluating and utilizing the sonnenbrand basalt aggregate clearer and more understandable, the present application is described in further detail below in conjunction with specific accompanying drawings and concrete embodiments.

DETAILED DESCRIPTION OF THE EMBODIMENTS

Figure 3:
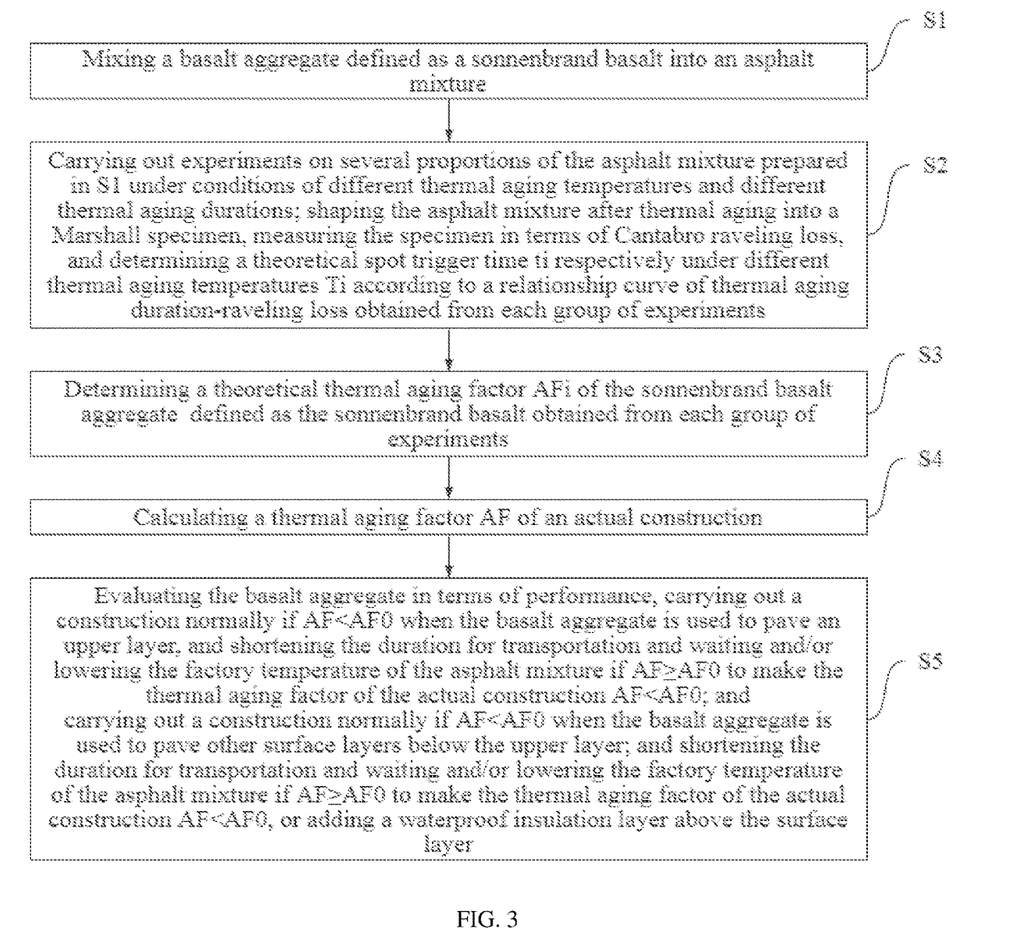
FIG. 3 illustrates a process of a method for evaluating and utilizing a sonnenbrand basalt aggregate according to an embodiment of the present application.

The present application provides a method for evaluating and utilizing a sonnenbrand basalt aggregate, including the following steps as shown in FIG. 3:

S1, mixing a basalt aggregate defined as a sonnenbrand basalt into an asphalt mixture;

S2, carrying out experiments on several proportions of the asphalt mixture prepared in the S1 under conditions of different thermal aging temperatures and different thermal aging durations, where the experiments are arranged with several groups, and the thermal aging temperatures of the experiments arranged with several groups are in a value range of 150 degrees Celsius (° C.)-190° C. and are selected at equal intervals within the value range of the temperatures, denoted as $T_i$, i=1, 2 . . . , n, and n is a number of experimental groups; in each group of the experiments, a thermal aging duration of each experiment is in a value range of 0 hour (h)-12 h, and is selected respectively at equal intervals within the value range; shaping the asphalt mixture after thermal aging into a Marshall specimen, measuring the specimen in terms of Cantabro raveling loss, and determining a theoretical spot trigger time $t_i$ respectively under different thermal aging temperatures $T_i$ according to a relationship curve of thermal aging duration-raveling loss obtained from each group of experiments;

S3, determining a theoretical thermal aging factor $AF_i$ of the basalt aggregate defined as the sonnenbrand basalt obtained from each group of experiments according to a calculation method as follows:

$$AF_i = T_i \times t_i$$

among them, $AF_i$ is a theoretical thermal aging factor obtained from an $i^{th}$ group experiment, i=1, 2 . . . , n, and n is the number of experimental groups; a minimum value of $AF_i$ is taken as a theoretical thermal aging factor $AF_0$ of the sonnenbrand phenomenon, where: $AF_0 = \min\{AF_1 \ldots AF_i \ldots AF_n\}$;

S4, calculating a thermal aging factor AF of an actual construction:

$$AF = T' \times t';$$

among them, T' is an average temperature value of a factory temperature of the actual construction of the asphalt mixture when a material truck leaves a mixing plant and an arrival temperature of the material truck after reaching a site and starting to pave, and t' is a duration for transportation and waiting for the material truck of the asphalt mixture from leaving a factory to arriving at the site to start paving;

S5, evaluating the basalt aggregate in terms of performance, carrying out a construction normally if $AF < AF_0$ when the basalt aggregate is used to pave an upper layer, and shortening the duration for transportation and waiting and lowering the factory temperature of the asphalt mixture if $AF \geq AF_0$ to make the thermal aging factor of the actual construction $AF < AF_0$; and when the basalt aggregate is used to pave other surface layers below the upper layer, carrying out a construction normally if $AF < AF_0$; and if $AF \geq AF_0$, shortening the duration for transportation and waiting and/or lowering the factory temperature of the asphalt mixture to make the thermal aging factor of the actual construction $AF < AF_0$, or adding a waterproof insulation layer above the surface layer.

Embodiment 1

Figure 4:
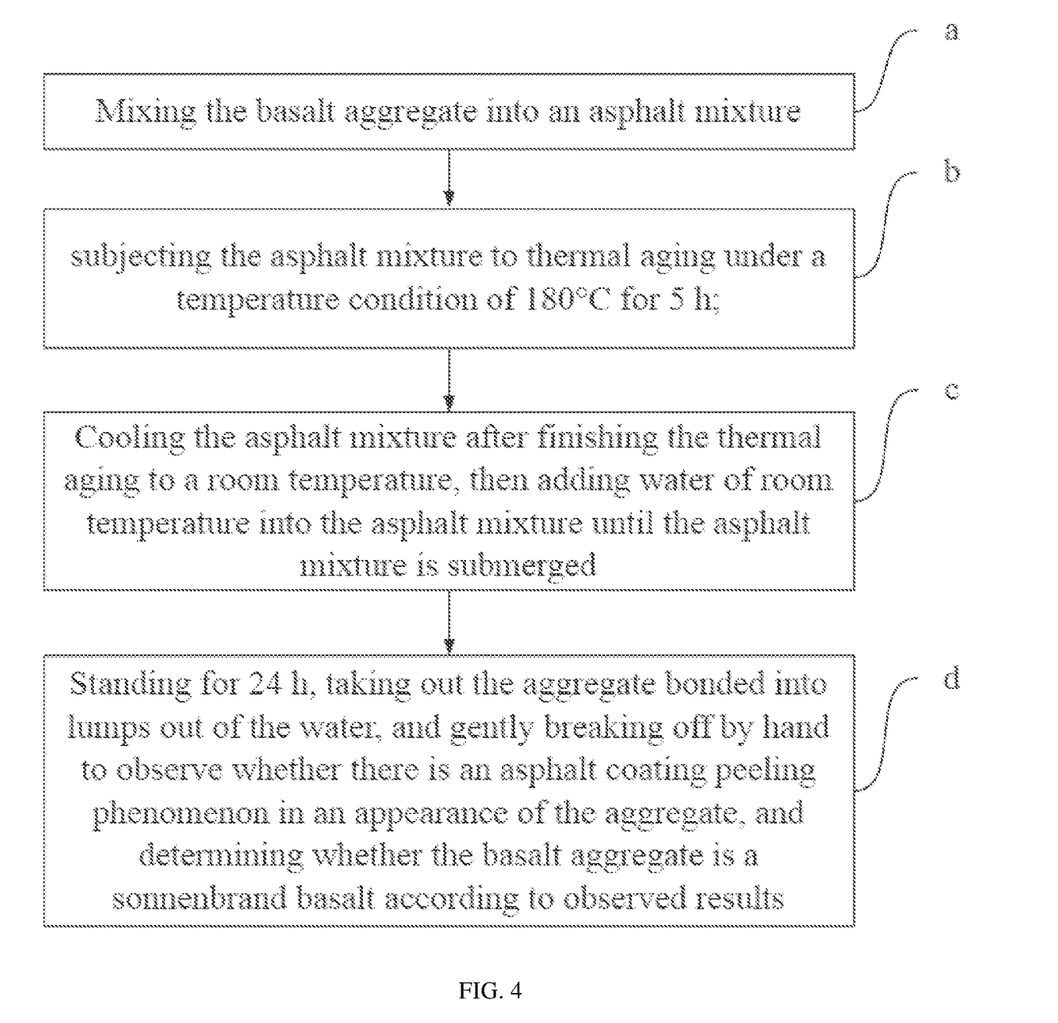
FIG. 4 shows a process of a method for defining a basalt aggregate according to an embodiment of the present application.

This embodiment provides a method for evaluating and utilizing a sonnenbrand basalt aggregate, which specifically includes the following steps:

(1) porous asphalt concrete (PAC) asphalt mixture is used in this embodiment; before construction, the basalt aggregate is defined with the following defining method as shown in FIG. 4:

a. mixing PAC with an oil-to-rock ratio of 4.9% and 0.1% polyester fiber incorporated in accordance with the PAC-13 production ratio (see Table 1) actually used in constructions;

TABLE 1

| | Gradation of PAC asphalt mixture | | | | | | | | |
|---|---|---|---|---|---|---|---|---|---|
| | Mass passage rate of passing through the following sieve holes (mm)/% | | | | | | | | |
| Mixture type | 16 | 13.2 | 9.5 | 4.75 | 2.36 | 1.18 | 0.6 | 0.3 | 0.15 | 0.075 |
| PAC-13 | 100 | 89.1 | 55.9 | 15.5 | 12.5 | 8.2 | 6.7 | 6.0 | 5.4 | 4.0 | b. evenly dispersing the asphalt mixture obtained by mixing in a tray, and placing the tray in an oven at 180° C. for thermal aging for 5 h;

c. taking the tray out of the oven, cooling the asphalt mixture to room temperature, and adding water of room temperature into the tray until the mixture is submerged; and d. standing the asphalt mixture for 24 hours (h), then taking out the aggregate bonded together into lumps from the tray, and breaking them lightly by hand to observe whether there is asphalt coating peeling phenomenon in the aggregate appearance, and determining that the basalt aggregate is sonnenbrand basalt when there is peeling phenomenon. In this embodiment, the asphalt coating peeling phenomenon is graded according to the asphalt coating peeling situation as observing whether there is asphalt coating peeling phenomenon in the aggregate appearance, see Table 2 for the grading standard.

TABLE 2

| Grade of asphalt coating peeling | |
|---|---|
| Asphalt peeling on aggregate surface after test | Adhesion grade |
| The asphalt coating is completely preserved, with a percentage of a peeled area close to 0. | 5 |
| The asphalt coating is moved by water in a few portions with an uneven thickness, and the percentage of peeled area is less than or equal to 10%. | 4 |
| The asphalt coating is obviously moved by water locally, basically retained on a surface of the aggregate, and the percentage of peeled area is less than or equal to 30%. | 3 |
| The asphalt coating is largely moved by water, partially remained on the surface of aggregate, and the percentage of the peeled area is greater than 30%. | 2 |
| The asphalt coating is completely moved by water, the aggregate is basically exposed, and the asphalt floats on the water surface. | 1 |

For observation, the percentage of peeled area is visually measured by two or more testers respectively, and the average value is taken as the test result; when the grade obtained from the test results is lower than grade 5, i.e., when the grade is determined to be 1-4, the basalt aggregate is judged to be a sonnenbrand basalt. The PAC asphalt mixture formulated in this embodiment has a severely peeled appearance of grade 2 and is diagnosed as a sonnenbrand basalt;

the PAC asphalt mixture of sonnenbrand basalt is still prepared according to the ratio in Table 1;

(2) part of the asphalt mixture to be used, prepared in step (1), is taken for experiments under different thermal aging temperatures and different thermal aging durations; in this embodiment, the experiments include 5 groups, and the thermal aging temperatures of the 5 groups of experiments are in the value range of 150° C.-190° C., which are selected at equal intervals within the value range, and are recorded as $T_i$, i=1, 2 . . . , 5; in this embodiment, $T_1$=150° C., $T_2$=160° C., $T_3$=170° C., $T_4$=180° C., $T_5$=190° C.; in each of the 5 groups of experiments, the value range of the thermal aging duration of each experiment is 0 h-12 h, which are selected at equal intervals within the value range of duration, and in this implementation, the thermal aging duration is set to 0 h, 1 h, 2 h, 3 h, 4 h, 5 h, 6 h, 12 h, i.e., each group of experiments includes 8 experiments.

Figure 1:
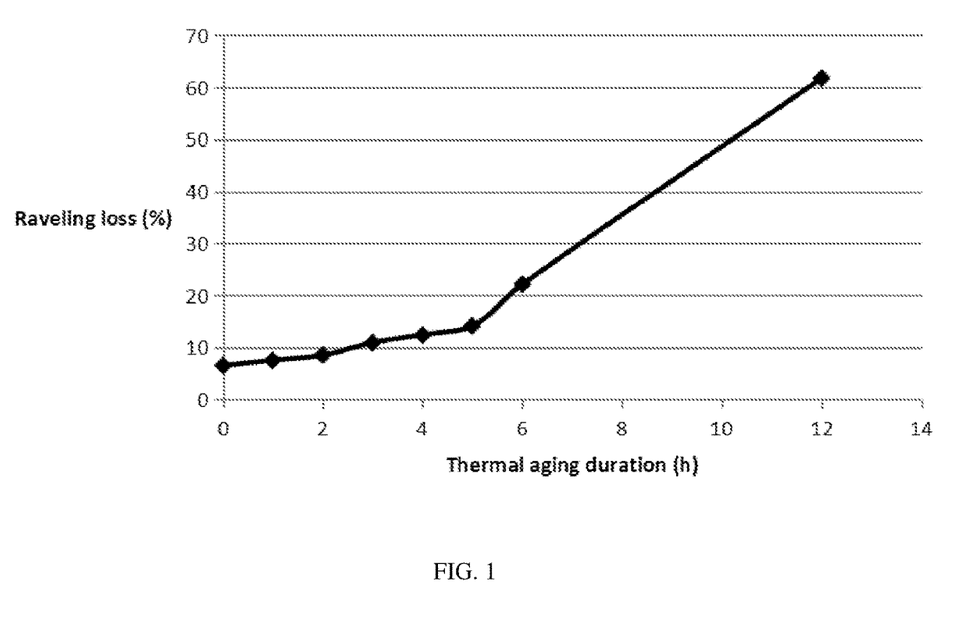
FIG. 1 shows a relationship diagram of thermal aging duration-raveling loss obtained from thermal aging experiments on a described porous asphalt concrete (PAC) asphalt mixture for different durations at the thermal aging temperature of 180 degrees Celsius (° C.) as described in the present application.

The asphalt mixture after thermal aging is molded into a Marshall specimen, and the Cantabro raveling loss of the specimen is tested, so as to obtain the relationship curves of thermal aging duration-raveling loss under different thermal aging temperatures $T_i$, respectively, and the theoretical spot triggering time $t_i$ is determined according to the curves, with a specific determination method as follows: when a raveling loss corresponding to an inflection point of a significantly increased raveling loss in the relationship curve of the thermal aging duration-raveling loss is ≤15%, the thermal aging duration corresponding to the inflection point is the theoretical spot trigger time $t_i$; and when the raveling loss corresponding to the inflection point of the significantly increased raveling loss in the relationship curve of the thermal aging duration-raveling loss is >15%, the thermal aging duration corresponding to the raveling loss of 15% is the theoretical spot trigger time $t_i$;

(3) the theoretical thermal aging factor $AF_i$ of the sonnenbrand basalt aggregate obtained from each group of experiments is calculated, and the calculation method is as follows:

$$AF_i = T_i \times t_i$$

among them, $AF_i$ is the theoretical thermal aging factor obtained from group i experiments, and i=1, 2 . . . , 5; the minimum value of $AF_i$ is taken as the theoretical thermal aging factor $AF_0$ of the basalt phenomenon, where:

$$AF_0 = \min\{AF_1 \ldots AF_i \ldots AF_n\}$$

in this embodiment, the minimum value of AFi is obtained from the fourth group of experiments, and the thermal aging duration-raveling loss relationship diagram of the fourth group of experiments is shown in FIG. 1; the theoretical triggering time $t_4$ of the sonnenbrand phenomenon in the fourth group of experiments is 5 h, and the corresponding raveling loss of asphalt mixture is 14.1%, less than 15%. In this embodiment, $AF_0$ is as follows:

$$AF_0 = AF_4 = T_4 \times t_4 = 180° C. \times 5h = 900° C. \cdot h$$

(4) the thermal aging factor of actual construction AF is calculated as:

$$AF = T' \times t'$$

among them, T' is an average temperature value of a factory temperature of the actual construction of the asphalt mixture when a material truck leaves a mixing plant and an arrival temperature of the material truck after reaching a site and starting to pave, and t' is a duration for transportation and waiting for the material truck of the asphalt mixture from leaving a mixing plant to arriving at the site to start paving;

statistics of the transportation and waiting duration t' of a material truck of PAC asphalt mixture for a physical project is 6 h, the average value of factory temperature $T_1$ when driving out of the mixing plant is 182° C., and the average value of arrival temperature $T_2$ when the material truck reaches the site and starts paving is 178° C.; the thermal aging factor AF=(178+182)×6/2=1080° C.·h is calculated for the actual construction;

(5) in this embodiment, the thermal aging factor in actual construction is AF>$AF_0$; the raveling loss of PAC asphalt mixture taken from the pavement site and tested by forming Marshall specimens indoors is 21.6%, the standard raveling loss of PAC asphalt mixture ≯ 15%, which indicates that the raveling loss of asphalt mixture has exceeded the standard, the road performance is significantly deteriorated and cannot be used directly.

To overcome the sonnenbrand phenomenon, the present embodiment reduces the production temperature of PAC asphalt mixture by mixing warm mixer. The amount of warm mixer blended in this embodiment is 5 weight percentage (wt %) of the asphalt mixture mass, so that the factory temperature $T_1$ when driving out of the mixing plant is 162° C. on average, and the arrival temperature $T_2$ when the material truck reaches the site and starts paving is 156° C. on average. In addition, the construction organization is optimized to shorten the engaging duration of construction, shorten the transportation and waiting duration t' to 5 h, and the thermal aging factor of the actual construction is calculated as AF=(156+162)×5/2=795° C.·h, AF<$AF_0$. The optimized PAC asphalt mixture is taken from the pavement site and tested again by forming Marshall specimens indoors, with a raveling loss of 11.8%, in compliance with the standard raveling loss of PAC asphalt mixture ≯ 15%, indicating that the pavement performance of the asphalt mixture has been significantly improved, and the sonnenbrand basalt is used according to the improved construction method.

Embodiment 2

The basalt aggregate and asphalt mixture used in this embodiment are exactly the same as in Embodiment 1, and steps (1)-(3) are the same as in Embodiment 1. In step (4) of the present embodiment, statistics of the transportation and waiting duration t' of a material truck of PAC asphalt mixture for a physical project is about 2 h, the average value of factory temperature $T_1$ when driving out of the mixing plant is 180° C., and the average value of arrival temperature $T_2$ when the material truck reaches the site and starts paving is 178° C.; the thermal aging factor AF=(178+180)×2/2=358° C.·h is calculated for the actual construction.

The thermal aging factor in actual construction is AF<$AF_0$; the raveling loss of PAC asphalt mixture taken from the pavement site and tested by forming Marshall specimens indoors is 11.2%, which is lower than the standard raveling loss of PAC asphalt mixture ≯ 15% and comparable to the raveling loss of fresh PAC asphalt mixture, indicating that the pavement performance of the asphalt mixture has no significant degradation and the light spot basalt may be used according to the existing construction method.

Embodiment 3

This embodiment provides a method for evaluating and utilizing sonnenbrand basalt aggregate, which specifically includes the following steps:

stone matrix asphalt (SMA) asphalt mixture is used in this embodiment; before construction, the basalt aggregate is defined with the following defining method:

a. mixing SMA with an oil-to-rock ratio of 6.0% and 0.3% lignin fiber incorporated in accordance with the SMA-13 production ratio (see Table 3) actually used in constructions;

TABLE 3

Gradation of SMA asphalt mixture

| | Mass passage rate of passing through the following sieve holes (mm)/% | | | | | | | | | |
|---|---|---|---|---|---|---|---|---|---|---|
| Mixture type | 16 | 13.2 | 9.5 | 4.75 | 2.36 | 1.18 | 0.6 | 0.3 | 0.15 | 0.075 |
| SMA-13 | 100 | 94.7 | 63.5 | 27.1 | 19.6 | 16.6 | 14.0 | 12.5 | 11.7 | 10.5 | b. evenly dispersing the asphalt mixture obtained by mixing in a tray, and placing the tray in an oven at 180° C. for thermal aging for 5 h;

c. taking the tray out of the oven, cooling the asphalt mixture to room temperature, and adding water of room temperature into the tray until the mixture is submerged; and d. standing the asphalt mixture for 24 hours (h), then taking out the aggregate bonded together into lumps from the tray, and breaking them lightly by hand to observe whether there is asphalt coating peeling phenomenon in the aggregate appearance, and determining that the basalt aggregate is sonnenbrand basalt when there is peeling phenomenon. In this embodiment, the asphalt coating peeling phenomenon is graded according to the asphalt coating peeling situation as observing whether there is asphalt coating peeling phenomenon in the aggregate appearance, see Table 4 for the grading standard.

TABLE 4

Grade of asphalt coating peeling

| Asphalt peeling on aggregate surface after test | Adhesion grade |
|---|---|
| The asphalt coating is completely preserved, with a percentage of a peeled area close to 0. | 5 |
| The asphalt coating is moved by water in a few portions with an uneven thickness, and the percentage of peeled area is less than or equal to 10%. | 4 |
| The asphalt coating is obviously moved by water locally, basically retained on a surface of the aggregate, and the percentage of peeled area is less than or equal to 30%. | 3 |
| The asphalt coating is largely moved by water, partially remained on the surface of aggregate, and the percentage of the peeled area is greater than 30%. | 2 |

TABLE 4-continued

Grade of asphalt coating peeling

| Asphalt peeling on aggregate surface after test | Adhesion grade |
|---|---|
| The asphalt coating is completely moved by water, the aggregate is basically exposed, and the asphalt floats on the water surface. | 1 |

For observation, the percentage of peeled area is visually measured by two or more testers respectively, and the average value is taken as the test result; when the grade obtained from the test results is lower than grade 5, i.e., when the grade is determined to be 1-4, the basalt aggregate is judged to be a sonnenbrand basalt. The SMA asphalt mixture formulated in this embodiment has a severely peeled appearance of grade 3 and is diagnosed as a sonnenbrand basalt;

the SMA asphalt mixture of sonnenbrand basalt is still prepared according to the ratio in Table 1;

part of the asphalt mixture to be used, prepared in step (1), is taken for experiments under different thermal aging temperatures and different thermal aging durations; in this embodiment, the experiments include 5 groups, and the thermal aging temperatures of the 5 groups of experiments are in the value range of 150° C.-190° C., which are selected at equal intervals within the value range, and are recorded as $T_i$, i=1, 2 . . . , 5; in this embodiment, $T_1$=150° C., $T_2$=160° C., $T_3$=170° C., $T_4$=180° C., $T_5$=190° C.; in each of the 5 groups of experiments, the value range of the thermal aging duration of each experiment is 0 h-12 h, which are selected at equal intervals within the value range of duration, and in this implementation, the thermal aging duration is set to 0 h, 1 h, 2 h, 3 h, 4 h, 5 h, 6 h, 12 h, i.e., each group of experiments includes 8 experiments.

Figure 2:
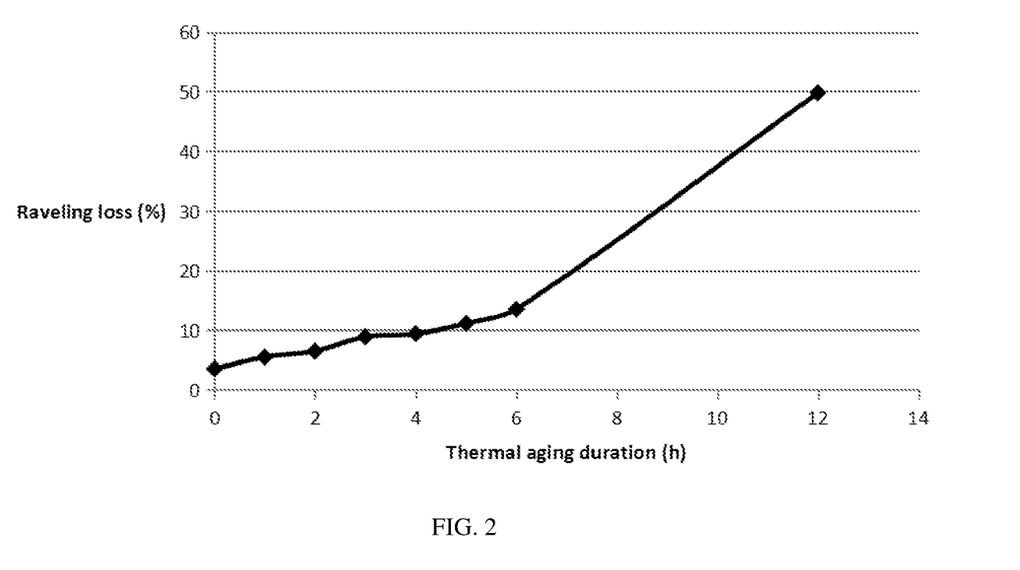
FIG. 2 shows a relationship diagram of thermal aging duration-raveling loss obtained from thermal aging experiments on a described stone matrix asphalt (SMA) asphalt mixture for different durations at the thermal aging temperature of 190° C. as described in the present application.

The asphalt mixture after thermal aging is molded into a Marshall specimen, and the Cantabro raveling loss of the specimen is tested, so as to obtain the relationship curves of thermal aging duration-raveling loss under different thermal aging temperatures $T_i$, respectively, and the theoretical spot triggering time $t_i$ is determined according to the curves, with a specific determination method as follows: when a raveling loss corresponding to an inflection point of a significantly increased raveling loss in the relationship curve of the thermal aging duration-raveling loss is ≤15%, the thermal aging duration corresponding to the inflection point is the theoretical spot trigger time $t_i$; and when the raveling loss corresponding to the inflection point of the significantly increased raveling loss in the relationship curve of the thermal aging duration-raveling loss is >15%, the thermal aging duration corresponding to the raveling loss of 15% is the theoretical spot trigger time $t_i$ (3) the theoretical thermal aging factor $AF_i$ of the sonnenbrand basalt aggregate obtained from each group of experiments is calculated, and the calculation method is as follows:

$$AF_i = T_i \times t_i$$

among them, $AF_i$ is the theoretical thermal aging factor obtained from group i experiments, and i=1, 2 . . . , 5; the minimum value of $AF_i$ is taken as the theoretical thermal aging factor $AF_0$ of the basalt phenomenon, where:

$$AF_0 = \min\{AF_1 \ldots AF_i \ldots AF_n\}$$

in this embodiment, the minimum value of $AF_i$ is obtained from the fifth group of experiments, and the thermal aging duration-raveling loss relationship diagram of the fifth group of experiments is shown in FIG. 2; the theoretical triggering time $t_5$ of the sonnenbrand phenomenon in the fifth group of experiments is 6 h, and the corresponding raveling loss of asphalt mixture is 13.5%, less than 15%. In this embodiment, $AF_0$ is as follows:

$$AF_0 = AF_5 = T_5 \times t_5 = 190° \text{ C.} \times 6h = 1140° \text{ C.·h}$$

(4) the thermal aging factor of actual construction AF is calculated as:

$$AF = T' \times t'$$

among them, T' is an average temperature value of a factory temperature of the actual construction of the asphalt mixture when a material truck leaves a mixing plant and an arrival temperature of the material truck after reaching a site and starting to pave, and t' is a duration for transportation and waiting for the material truck of the asphalt mixture from the mixing plant to the site to start paving;

statistics of the transportation and waiting duration t' of a material truck of SMA asphalt mixture for a physical project is 6 h, the average value of factory temperature $T_1$ when driving out of the mixing plant is 180° C., and the average value of arrival temperature $T_2$ when the material truck reaches the site and starts paving is 174° C.; the thermal aging factor AF=(180+174)×6/2=1062° C.·h is calculated for the actual construction;

(5) in this embodiment, the thermal aging factor in actual construction is AF<$AF_0$; the raveling loss of SMA asphalt mixture taken from the pavement site and tested by forming Marshall specimens indoors is 13.5%, the standard raveling loss of SMA asphalt mixture ≯ 15%, which indicates that the raveling loss of asphalt mixture has not exceeded the standard, there is no significant deterioration of the road performance and can be used directly.

Embodiment 4

The basalt aggregate and asphalt mixture used in this embodiment are exactly the same as in Embodiment 3, and steps (1)-(3) are the same as in Embodiment 1. In step (4) of the present embodiment, statistics of the transportation and waiting duration t' of a material truck of PAC asphalt mixture for a physical project is about 10 h, the average value of factory temperature $T_1$ when driving out of the mixing plant is 180° C., and the average value of arrival temperature $T_2$ when the material truck reaches the site and starts paving is 170° C.; the thermal aging factor AF=(180+170)×10/2=1750° C.·h is calculated for the actual construction.

The actual construction thermal aging factor $AF_0$<AF. The SMA asphalt mixture was taken from the pavement site and tested in the forming Marshall specimens indoors with a raveling loss of 36.5%, which is greater than the standard raveling loss of SMA asphalt mixture ≯ 15%, indicating that the road performance of the asphalt mixture has significantly deteriorated and cannot be used directly. By adjusting the designing scheme, the asphalt mixture is paved in the middle surface layer of the emergency lane, and a 0.5 cm of rock wool layer and 1 cm of rubberized asphalt gravel sealing layer are paved between the middle surface layer and the upper layer in order from the bottom to the top as a thermal insulation layer and waterproof layer. The additional insulation layer and waterproof layer can improve the performance of the surface layer of light spot basalt aggregate, and the additional layers are suitable for use in the case of $AF_0$<AF<$AF_{max}$, where $AF_{max}$, preferably, is 2160° C.·h.

Embodiment 5

The basalt aggregate and asphalt mixture used in this embodiment are exactly the same as in Embodiment 3, and steps (1)-(3) are the same as in Embodiment 1. In step (4) of the present embodiment, statistics of the transportation and waiting duration t' of a material truck of PAC asphalt mixture for a physical project is about 24 h, the average value of factory temperature $T_1$ when driving out of the mixing plant is 180° C., and the average value of arrival temperature $T_2$ when the material truck reaches the site and starts paving is 150° C.; the thermal aging factor $AF=(180+150)\times24/2=3960°$ C.·h is calculated for the actual construction.

The actual construction thermal aging factor $AF>AF_{max}$, $AF_{max}=2160°$ C.·h. SMA asphalt mixture is taken from the pavement site and tested by forming Marshall specimens indoors with a raveling loss close to 100%, and no complete residual specimens is found, the raveling loss is much greater than the SMA asphalt mixture standard ≯ 15%, indicating that the road performance of the asphalt mixture has been significantly deteriorated and therefore the SMA asphalt mixture cannot be used directly. The production temperature of SMA asphalt mixture needs to be lowered by adding warm mixer; if no measures are taken, the SMA asphalt mixture may only be discarded.

The pavement performance after construction of basalt aggregates in Embodiments 1-5 above is shown in the following table:

| | | | Pavement damage state | |
| --- | --- | --- | --- | --- |
| | Measures | Thermal aging factor | During construction | Within a short period of opening to traffic (completion acceptance) | 2 years after opening to traffic (completion acceptance) |
| Embodiment 1 | Warm mixing + shortened waiting duraiton | $AF < AF_0$ | No obvious damage | No obvious damage | No obvious damage |
| Embodiment 2 | No measures have been taken | $AF < AF_0$ | No obvious damage | No obvious damage | No obvious damage |
| Embodiment 3 | No measures have been taken | $AF < AF_0$ | No obvious damage | No obvious damage | No obvious damage |
| Embodiment 4 | Adding waterproof and insulation layers | $AF_0 < AF < AF_{max}$ | No obvious damage | No obvious damage | No obvious damage |
| Embodiment 5 | No measures have been taken | $AF > AF_{max}$ | The asphalt mixture is discarded and unused. | | |

COMPARATIVE EMBODIMENTS

The comparative embodiments are provided for further illustrating the technical effectiveness of the method of diagnosis and evaluation described in the present application.

Comparative Embodiment 1

Basalt aggregates are tested for mass loss, abrasion value loss, and impact value loss after 36 h of continuous boiling according to the EU standard BS EN 1367-3:2001 Tests for thermal and weathering properties of aggregates: Part 3: Boiling test for Sonnenbrand basalt, with test results as shown in Table 5. According to the existing evaluation method, the basalt aggregate is a sonnenbrand basalt.

TABLE 5

Performance of basalt aggregate after continuous boiling for 36 h

| Test index | Unit | Test result | Technical requirement | Time-consumed for diagnosis | Diagnostic conclusion |
| --- | --- | --- | --- | --- | --- |
| Mass loss | % | 1.5 | ≤1 | Not less than 3 days | sonnenbrand basalt |
| Abrasion value loss | % | 10.6 | ≤8 | | |
| Impact value loss | % | 8.3 | ≤5 | | |

Comparative Embodiment 2

When diagnosing the same basalt aggregate as in embodiment 1, this comparative embodiment mixes PAC asphalt mixture according to the PAC-13 production ratio (see Table 1) actually used in the project, with an oil-to-rock ratio of 4.9% and 0.1% polyester fiber incorporated. The asphalt mixture is evenly dispersed in a tray, after the asphalt mixture is cooled to room temperature, water of room temperature is added into the tray until the mixture is submerged; the asphalt mixture is stood for 24 h, then the aggregate that bonded together into lumps are taken out from the tray, and broken lightly by hand to observe whether there is asphalt coating peeling phenomenon in the aggregate appearance.

Comparative Embodiment 3

This comparative embodiment uses the same production ratio of PAC-13 (see Table 1) to mix PAC asphalt mixture with an oil-to-rock ratio of 4.9% and 0.1% polyester fibers when diagnosing the same basalt aggregate as in Embodiment 1. The mixture is evenly dispersed in a tray placed in a 180° C. oven for thermal aging of 5 h; the tray is then removed from the oven, the mixture is allowed to stand for 24 h, and the aggregate lumps bonded together are removed from the tray and lightly broken by hand to observe the appearance of the aggregate to see if the asphalt coating is peeled off. The appearance of the aggregates in Comparative embodiment 2 and Comparative embodiment 3 is observed, and it is found that there is no asphalt coating peeling in Comparative embodiment 2 that has not undergone high-temperature thermal aging and water immersion. The appearance of the aggregates in Comparative embodiment 3, which underwent high-temperature thermal aging, shows a slight peeling of asphalt coating, which is Grade 4. While the aggregate in the embodiment 1 shows severe asphalt coating peeling in appearance as grade 2 after the aggregate undergoes high temperature thermal aging and water immersion. By using the diagnosis method of basalt aggregate sonnenbrand phenomenon proposed in this application, the asphalt coating peeling after thermal aging and water immersion is quickly and accurately diagnosed.

In addition, the sonnenbrand of basalt aggregate is not diagnosed in Comparative embodiment 2, and the sonnenbrand phenomenon of basalt aggregate is diagnosed in Comparative embodiment 3, but the rating is 4, with a small asphalt coating peeling area, which is subject to human judgment as well as repetition error and reproducibility error, and is prone to the problem that the rating is 5 and the sonnenbrand phenomenon cannot be diagnosed. Embodiment 1 is graded as 2, showing significant asphalt coating peeling, accurately diagnosing the light spot phenomenon in basalt aggregates, and taking a total duration of about 36 h. Compared to Comparative embodiment 1, the diagnostic conclusion is the same, but the time consumption is substantially reduced and the operation is increasingly easy.

Comparative Embodiment 4

The PAC asphalt mixture blended in Embodiment 1 is evaluated using existing evaluation methods: without any thermal aging treatment, the raveling loss of the mixture is tested according to standard test methods, and the result is 8.2%, which is smaller than the technical requirement of 15%, so it is directly paved in the physical project without using measures such as temperature reduction and shortening the transportation duration. When the asphalt mixture is paved and compacted, the peeling of the asphalt coating appears at the location where the rubber wheel stays in the process of rolling by the rubber wheel roller. In the next day of traffic marking, the location where the marking vehicle turnaround appears a significant amount of asphalt coating peeling phenomenon. After three days of opening for traffic operation, the construction section shows a serious problem of aggregate dislodgement at certain locations, so the construction section is subjected to rework. According to the Highway Performance Assessment Standards (JTG 5210-2018), the pavement breakage rate exceeds 2% and the rating is only medium.

In the case of Embodiment 1 of this application, the construction quality of PAC asphalt mixture is effectively ensured after adopting measures such as temperature lowering and shortening the transportation duration, and no asphalt coating peeling occurs during the whole construction process and the 2-year operation phase. According to the Highway Performance Assessment Standards (JTG 5210-2018), the pavement breakage rate is less than 2% and the rating is excellent.

Comparative Embodiment 5

The SMA asphalt mixture of Embodiment 4 is paved in the physical project in the middle layer, with no additional waterproof layer and insulation layer; in the short period of opening to traffic, no obvious phenomenon of asphalt coating peeling or aggregate dislodging occurs. However, in 2 years of operation for completion acceptance, a serious aggregate shedding phenomenon occurs in certain locations of this construction section. According to the Highway Performance Assessment Standards (JTG 5210-2018), the pavement breakage rate exceeds 2% and the rating is only medium.

In the case of Embodiment 4 of this application, the construction quality of SMA asphalt mixture is effectively ensured after adopting measures of additional waterproof layer and insulation layer, and no asphalt coating peeling phenomenon occurs throughout the construction process and 2 years of opening to traffic operation.

Comparative Embodiment 6

The SMA asphalt mixture in Embodiment 5 suffers a significant deterioration in performance due to severe thermal aging effects. The SMA asphalt mixture of Embodiment 5 is paved in the physical project, and within a short period of opening to traffic and operation, serious aggregate dislodgement occurs in certain locations of this construction section. According to the Highway Performance Assessment Standards (JTG 5210-2018), the pavement breakage rate exceeds 2% and the rating is only medium.

TABLE 6

Pavement damage status after construction in Comparative embodiments 4-6

| | | | | Pavement damage state | |
|---|---|---|---|---|---|
| Cases | Measures | Thermal aging factor | construction period | Within a short period of opening to traffic (completion acceptance) | 2 years after opening to traffic (completion acceptance) |
| Comparative embodiment 4 | No measures have been taken | $AF_0 <$ $AF < AF_{max}$ | Peeling of asphalt coating | Aggregate falls off at certain positions and is reworked | — |
| Comparative embodiment 5 | No measures have been taken | $AF_0 <$ $AF < AF_{max}$ | No obvious damage | No obvious damage | Aggregate falls off at certain positions and is reworked |
| Comparative embodiment 6 | No measures have been taken | $AF > AF_{max}$ | No obvious damage | Aggregate falls off at certain positions and is reworked | — |

The above embodiments are only several embodiments of the present application with a rather specific and detailed description, but they should not be construed as a limitation of the patent scope of the present application. It should be noted that for a person of ordinary skill in the art, several deformations and improvements may be made without departing from the conception of the present application, all of which belong to the scope of protection of the present application. Therefore, the scope of protection of the present application shall be subject to the claims.

What is claimed is:

1. A method for evaluating and utilizing a sonnenbrand basalt aggregate, comprising following steps:
    (1) mixing a basalt aggregate defined as a sonnenbrand basalt into an asphalt mixture, wherein, a. mixing the basalt aggregate into an asphalt mixture; b. subjecting the asphalt mixture to thermal aging under a temperature condition of 180 degrees Celsius for 5 hours; c. cooling the asphalt mixture after finishing the thermal aging to a room temperature, then adding water of room temperature into the asphalt mixture until the asphalt mixture is submerged; and d. standing for 24 hours, taking out the aggregate bonded into lumps out of the water, and gently breaking off by hand to observe whether there is an asphalt coating peeling phenomenon in an appearance of the aggregate, and determining whether the basalt aggregate is a sonnenbrand basalt according to observed results;
    (2) carrying out experiments on several proportions of the asphalt mixture prepared in the step (1) under conditions of different thermal aging temperatures and different thermal aging durations, wherein the experiments are arranged with several groups, and the thermal aging temperatures of the experiments arranged with the several groups are in a value range of 150 degrees Celsius-190 degrees Celsius and are selected at equal intervals within the value range of the temperatures, denoted as $T1$, $i=1, 2 \ldots, n$, and n is a number of experimental groups; in each group of the experiments, a thermal aging duration of each of the experiments is in a value range of 0 hour-12 hours, and is selected respectively at equal intervals within the value range;

shaping the asphalt mixture after thermal aging into a Marshall specimen, measuring the specimen in terms of Cantabro raveling loss, and determining a theoretical spot trigger time $ti$ respectively under different thermal aging temperatures $Ti$ according to a relationship curve of thermal aging duration-raveling loss obtained from each group of experiments; wherein a method for determining the theoretical spot trigger time $ti$ is: when a raveling loss corresponding to an inflection point of a significantly increased raveling loss in the relationship curve of the thermal aging duration-raveling loss is ≤15%, the thermal aging duration corresponding to the inflection point is the theoretical spot trigger time $ti$; and when the raveling loss corresponding to the inflection point of the significantly increased raveling loss in the relationship curve of the thermal aging duration-raveling loss is >15%, the thermal aging duration corresponding to the raveling loss of 15% is the theoretical spot trigger time $ti$;

(3) determining a theoretical thermal aging factor $AFi$ of a sonnenbrand basalt aggregate obtained from each group of experiments according to a calculation method:

$$AFi = Ti \times ti$$

wherein $AFi$ is a theoretical thermal aging factor obtained from an ith group experiment, $i=1, 2 \ldots, n$, and n is a number of experimental groups; a minimum value of $AFi$ is taken as a theoretical thermal aging factor $AF0$ of sonnenbrand phenomenon:

$$AF0 = \min \{[\![AF]\!]\_1 \ldots [\![AF]\!]\_i \ldots [\![AF]\!]\_n\}$$

(4) calculating a thermal aging factor $AF$ of an actual construction:

$$AF = T' \times t'$$

wherein $T'$ is an average temperature value of a factory temperature of the actual construction of the asphalt mixture when a material truck leaves a mixing plant and an arrival temperature of the material truck after reaching a site and starting to pave, and $t'$ is a duration for transportation and waiting for the material truck of the asphalt mixture from leaving a mixing plant to arriving at the site to start paving; and (5) evaluating the basalt aggregate in terms of performance, carrying out a construction normally if $AF<AF0$ when the basalt aggregate is used to pave an upper layer, and shortening the duration for transportation and waiting and lowering the factory temperature of the asphalt mixture if $AF \geq AF0$ to make the thermal aging factor of the actual construction $AF<AF0$; and when the basalt aggregate is used to pave other surface layers below the upper layer, carrying out a construction normally if $AF<AF0$; and if $AF \geq AF0$, shortening the duration for transportation and waiting and/or lowering the factory temperature of the asphalt mixture to make the thermal aging factor of the actual construction $AF<AF0$, or adding a waterproof insulation layer above the surface layer.

2. The method for evaluating and utilizing sonnenbrand basalt aggregate according to claim 1, wherein as observing whether there is the asphalt coating peeling phenomenon on the appearance of the aggregate, the asphalt coating peeling phenomenon is graded according to a peeling situation of the asphalt coating, with a grading criteria of: grade 5: the asphalt coating is completely preserved, with a percentage of a peeled area close to 0; grade 4: the asphalt coating is moved by water in a few portions with an uneven thickness, and the percentage of peeled area is less than or equal to 10%; grade 3: the asphalt coating is obviously moved by water locally, basically retained on a surface of the aggregate, and the percentage of peeled area is less than or equal to 30%; grade 2: the asphalt coating is largely moved by water, partially remained on the surface of aggregate, and the percentage of the peeled area is greater than 30%; and grade 1: the asphalt coating is completely moved by water, the aggregate is basically exposed, and the asphalt floats on a water surface; the basalt aggregate is defined as a sonnenbrand basalt if the grade is below 5.

3. The method for evaluating and utilizing sonnenbrand basalt aggregate according to claim 1, wherein in the step (1), when mixing the basalt aggregate defined as sonnenbrand basalt into the asphalt mixture, a production mixture ratio adopted in actual construction is used for mixing.

4. The method for evaluating and utilizing sonnenbrand basalt aggregate according to claim 3, wherein the asphalt mixture mixed in the step (1) is any one of asphalt concrete (AC) mixture, stone matrix asphalt (SMA), open-graded friction course (OGFC) porous asphalt mixture or porous asphalt concrete (PAC) asphalt mixture.

5. The method for evaluating and utilizing sonnenbrand basalt aggregate according to claim 4, wherein in the step (5), as lowering the factory temperature of the asphalt mixture, the factory temperature of the asphalt mixture is lowered by using a warm-mixing technology.

6. The method for evaluating and utilizing sonnenbrand basalt aggregate according to claim 5, wherein the waterproof insulation layer comprises a double-layer structure of a waterproof layer and a thermal insulation layer.

7. The method for evaluating and utilizing sonnenbrand basalt aggregate according to claim 6, wherein the waterproof layer is any one of emulsified asphalt, hot asphalt, hot asphalt macadam sealing layer and polymer material paving layer.

8. The method for evaluating and utilizing sonnenbrand basalt aggregate according to claim 7, wherein the insulation layer is any one of material laying layers such as rubber, ceramic, rock wool, fiber, foam board.

* * * * *